US00PP10437P

United States Patent [19]

Glaser

[11] Patent Number: Plant 10,437

[45] Date of Patent: Jun. 9, 1998

[54] AZALEA PLANT NAMED KOSMOS

[76] Inventor: Karl Glaser, Alte Strasse 9, D-64832 Babenhausen, Germany

[21] Appl. No.: 651,732

[22] Filed: May 22, 1996

[51] Int. Cl.[6] ..... A01H 5/00

[52] U.S. Cl. ..... Plt./57

[58] Field of Search ..... Plt./57

[56] References Cited

PUBLICATIONS

Bettin et al. Supplementary lighting for azaleas. Deutsher Gartenbau. vol. 44 (19): pp. 1262–1263, 1990.

*Primary Examiner*—James R. Feyrer
*Assistant Examiner*—Melissa L. Kimball
*Attorney, Agent, or Firm*—Foley & Lardner

[57] ABSTRACT

An azalea plant named Kosmos particularly characterized by its evergreen foliage, semi-double flower form with ruffled petal margins, dark pink flower cooler, free branching, compact semi-upright plant habit, uniform flowering response in a year round controlled program, and by its good cooler tolerance and keeping quality.

1 Drawing Sheet

The present invention comprises a new and distinct cultivar of Azalea, a greenhouse forcing type, hereinafter referred to as Kosmos.

Kosmos, identified as Code 2-1 during the selection process, originated from a planned cross hybridization between two selected breeding lines in a controlled breading program in Babenhausen, Germany by the inventor Karl Glaser.

The female, or seed parent of Kosmos is an unnamed seedling with a large pink single shaped flower, a round growth habit, and dark green foliage. The male, or pollen parent is an unnamed seedling with a red funnel-shaped flower, a round growth habit, and medium green foliage.

Kosmos was discovered and selected as one flowering plant within the progeny of the stated cross by the inventor Karl Glaser in January 1982 in Babenhausen, Germany.

The first asexual reproduction of Kosmos was accomplished when vegetative cuttings were taken from the initial selection in April 1982, in Babenhausen, Germany, by technicians working under formulations established and supervised by Karl Glaser.

Horticultural examination of controlled flowerings of successive generations of plants derived from cuttings taken from the original selection has shown that the unique combination of characteristics as herein disclosed for Kosmos are fixed and retained through successive generations of asexual reproduction.

Kosmos has not been observed under all possible environmental conditions. The phenotype may vary significantly with variations in environment such as temperature, light intensity and day length without, however, any variance in the genotype.

The following observations, measurements and comparisons describe plants that were grown in Salinas, Calif. in a controlled greenhouse environment and following a commercial schedule.

The following traits have been repeatedly observed and are determined to be basic characteristics of Kosmos, which in combination distinguish this azalea as a new and distinct cultivar:

1. Dark pink flower color.
2. Semi-double flowers ranging in size from 8.5 to 11.0cm in diameter, with 10.0cm the average size.
3. Flowers have ruffled margins.
4. Compact, semi-upright and freely branching plant habit.

5. Uniform response in year round controlled flowering programs, forcing in 36 days on average.
6. Long lasting flowers, with flowers in a simulated home environment lasting up to two weeks.
7. Medium green glossy evergreen foliage, leathery in appearance.
8. Good foliage retention and no flower bud damage when cooled for six weeks with no lighting at 38 degrees F.

The accompanying color photograph shows in perspective view the unique features of the new cultivar, with colors being as true as possible with color illustrations of this type.

Of the commercial cultivars known to the inventor, the most similar in comparison to Kosmos is the variety Solitaire, disclosed in U.S. Plant Pat. No. 3,171. Flower color and flower response are similar. Kosmos differs from Solitaire in that Kosmos has ruffled petal margins, larger flowers, and foliage which is darker green and larger.

In the following description color references are made to The Royal Horticultural Society Colour Chart. The color values were determined on Apr. 20, 1995. All readings were taken in an office under cool white fluorescent lights, facing a west window between the hours of 10:00 A.M. and 2:00 P.M.

Classification:

*Botanical.*—Rhododendron hybrida, evergreen type c.v. 'Kosmos'.

*Commercial.*—Florist forcing pot azalea.

Inflorescence

A. Flower (General):

*Size.*—8.5 to 11cm.

*Borne.*—Terminal cluster, usually 3 per bud, ranging from 2–4.

*Form.*—Semi-double funnel-form.

*Blooming habit.*—Buds easily and uniformly in a year round program. The majority of terminal budes break color within one week of the first. Flowering begins approximately 36 days after the start of forcing.

*Fragrance.*—None.

B. Corolla (Petals):

*Texture.*—Soft.

*Substance.*—Heavy.

*Shape.*—Rounded with ruffled margins.

*Color (fully open).*—Generally between 57D and 67C as flowers age.

*Upper surface.*—Generally between 57D and 67C, and 66C.

*Lower surface.*—67C.

*Blotch.*—60B.

C. Bud:

*Size*—Medium.

*Shape.*—Conoidal.

*Color.*—67C.

*Bud sheath.*—Immature: Light green with light brown hairs. Mature: Brown with light brown hairs.

D. Calyx:

*Form.*—Rounded.

*Color.*—144A.

E. Peduncle:

*Length.*—0.4 to 1.4cm.

*Strength.*—Strong.

*Aspect.*—Pubescent.

F. Reproductive organs:

*Androecium (stamens).*—Number: 0 to 5. Many are fully or partially petaloid. Anthers: 58C; often missing, with the filaments joining with the petals. Filaments: Length: 0.0 to 2.4cm. Color: 58D.

*Gynoecium (pistil).*—Stigma: 64A. Style: Length: 1.0 to 3.6cm. Color: 63A initially, maturing to 58B Ovary: Pubescent.

Plant Characteristics

A. Foliage;

*Type.*—Evergreen.

*Arrangement.*—Alternate.

*Shape.*—Elliptic.

*Size.*—Length: 1.9 to 6.8cm. Width: 1.0 to 3.6cm.

*Margin.*—Entire.

*Color.*—Immature: Upper Surface: 144A Lower Surface: Between 144A and 144B Mature: Upper Surface: 147A Lower Surface 146B Texture: Leathery Tomentum: Present on upper surface. Insignificant.

B. Stems:

*Color.*—Immature: 166B. Mature: 166A.

C. Plant habit: Compact, semi-upright bush which achieves a uniform, symmetrical plant in a 6" pot when pinched 3 times. Total crop time to dormant budded stage is 40–42 weeks to produce a plant approximately 26–34cm in diameter and 36cm in height. Internode lengths vary from 2 to 25mm on the same stem.

D. Branching habit: Free branching, producing 2–3 breaks when a vegatative cutting is pinched.

E. Rooting: Roots easily in 8 to 10 weeks with 75 degrees F. temperature.

F. Budding ease: Plants produce flower buds easily and uniformly year round with the use of commercially available growth regulators. Kosmos has a middle natural season response time.

G. Cooler tolerance: Plants packed in a cooler as a means of breaking dormancy perform well. Kosmos is tolerant of six weeks in an unlighted cooler at 38 degrees F. without foliage loss or bud damage.

H. Blooming: Plants reach the stage of 12 buds showing color in 36 days on average after the cooling treament. This varies from 24 to 40 days depending upon temperature and stage of flower bud development at the start of forcing. Kosmos flowers uniformly and profusely across the plant and down the sides.

I. Shelf life: When plants are moved to an office or home environment at the stage of eight open flowers, they maintain an attractive appearance for up to two weeks on average. Flowers are somewhat persistent, only occasionally dropping as flowers become old.

I claim:

1. A new and distinct cultivar of azalea plant named Kosmos, as described and illustrated.

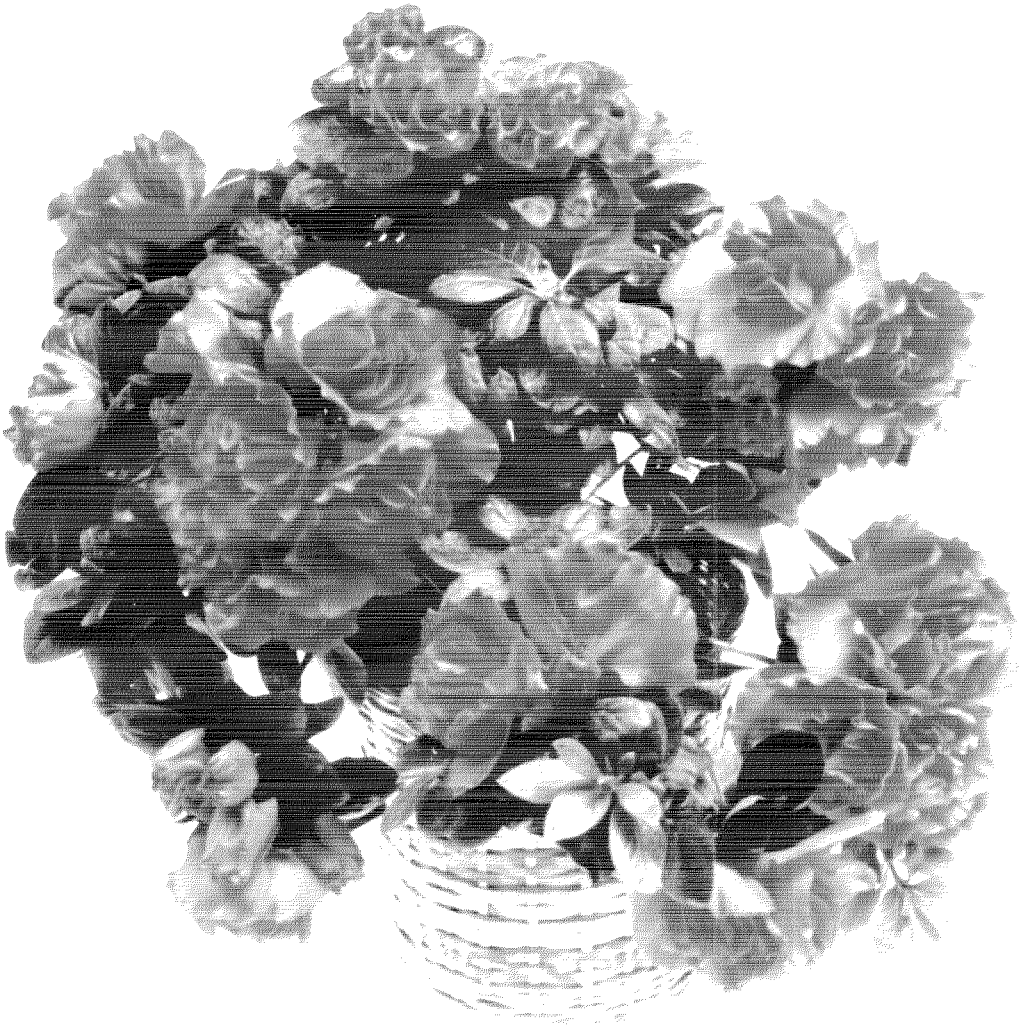

* * * * *